United States Patent [19]

Priegnitz

[11] 4,333,740
[45] Jun. 8, 1982

[54] PROCESS FOR THE SEPARATION OF WATER FROM ETHANOL

[75] Inventor: James W. Priegnitz, Elgin, Ill.

[73] Assignee: UOP Inc., Des Plaines, Ill.

[21] Appl. No.: 219,746

[22] Filed: Dec. 23, 1980

[51] Int. Cl.$^3$ .................. C10L 1/02; C07C 29/76
[52] U.S. Cl. ........................... 44/56; 568/916
[58] Field of Search ............. 568/916, 917; 44/56

[56] References Cited

U.S. PATENT DOCUMENTS

| | | | |
|---|---|---|---|
| 1,413,864 | 4/1922 | Mann, Jr. ........................ | 568/917 |
| 2,985,589 | 5/1961 | Broughton et al. .............. | 210/34 |
| 3,114,782 | 12/1963 | Fleck et al. ..................... | 260/674 |
| 3,201,491 | 8/1965 | Stine et al. ..................... | 260/676 |
| 3,235,610 | 2/1966 | Wymore .......................... | 568/916 |
| 3,265,750 | 8/1966 | Peck et al. ...................... | 260/666 |
| 3,510,423 | 5/1970 | Neuzil et al. ................... | 208/310 |
| 3,558,732 | 1/1971 | Neuzil ............................. | 260/674 |
| 3,668,267 | 6/1972 | Hedge ............................. | 260/674 |
| 3,686,342 | 8/1972 | Neuzil ............................. | 260/674 |
| 3,997,620 | 12/1976 | Neuzil ............................. | 260/674 |
| 4,273,621 | 6/1981 | Forhoff ........................... | 568/916 |

OTHER PUBLICATIONS

Chemical Engineering, Nov. 27, 1980, p. 103.

*Primary Examiner*—Joseph E. Evans
*Attorney, Agent, or Firm*—James R. Hoatson, Jr.; Louis A. Morris; William H. Page II

[57] ABSTRACT

An adsorptive separation process for separating water from a feed mixture comprising ethanol and water, which process comprises contacting the feed mixture with an adsorbent comprising corn meal, selectively adsorbing substantially all of the water to be separated to the substantial exclusion of the ethanol and thereafter recovering high purity ethanol. The used corn meal may be fermented to provide a source of ethanol. The process may employ a countercurrent moving bed or simulated moving bed countercurrent flow system.

17 Claims, 3 Drawing Figures

4,333,740

PROCESS FOR THE SEPARATION OF WATER FROM ETHANOL

BACKGROUND OF THE INVENTION

1. Field of the Invention

The field of art to which the claimed invention pertains is solid bed adsorptive separation. More specifically, the claimed invention relates to a process for the separation of water from a feed mixture comprising ethanol and water which process employs a solid adsorbent which selectively removes the water from the feed mixture.

2. Description of the Prior Art

Diminishing world supplies and availability of crude oil as well as sporadic regional shortfalls of gasoline for motor fuel have created considerable incentive for the development and use of alternative fuels. Ethanol is gaining wide popularity as such a fuel, particularly when mixed with gasoline to form a mixture known as gasohol. Gasohol may contain up to about 10 vol. % ethanol, without modifications to presently used automobile engines being required, thereby extending the volume of motor fuel availability by a like percentage.

The primary source of the ethanol used in gasohol is derived primarily from the fermentation of mash, usually from corn. Natural fermentation is able to produce an ethanol-water product mixture containing at the most about 12 vol. % ethanol. This mixture may easily be concentrated by distillation to about 95% ethanol. Higher concentrations of ethanol, however, as required in gasohol are obtained only by expenditures of great amounts of energy and great difficulty due to the formation of an ethanol-water azeotrope at about the 95% ethanol concentration. A means of achieving the greater than 95% ethanol concentration without such a great expenditure of energy would thus be extremely valuable. One, therefore, might consider the many known adsorptive separation processes known in the art for possible application to the separation of ethanol from water.

For example, it is well-known in the separation art that certain crystalline aluminosilicates can be used to separate hydrocarbon species from mixtures thereof. The separation of normal paraffins from branched chain paraffins, for example, can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423, for example, disclose processes in which large pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes. In processes described in U.S. Pat. Nos. 3,558,732, 3,686,342 and 3,997,620, adsorbents comprising particular zeolites are used to separate para-xylene from feed mixtures comprising para-xylene over the other xylene isomers. In the last mentioned processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. Also, in the last mentioned processes the adsorption and desorption may be continuously carried out in a simulated moving bed countercurrent flow system, the operating principles and sequence of which are described in U.S. Pat. No. 2,985,589.

Any of the above adsorbents of the above processes might be effective for the separation of water from ethanol since all of those adsorbents are hydrophilic, i.e. they would probably be selective for water over the ethanol. However, there would be the problem of what could be used as an effective desorbent. The separation of the desorbent, if possible, from the ethanol raffinate and water extract would be considerably more costly than the primary distillation of the alcohol from the water.

We have discovered an adsorbent selective for water over ethanol which may be used in a process not requiring a desorption step and which is itself a source of ethanol.

SUMMARY OF THE INVENTION

In brief summary, the present invention is, in one embodiment, a process for separating water from a feed mixture comprising ethanol and water. The process comprises contacting, at adsorption conditions, the mixture with an adsorbent comprising corn meal, and selectively adsorbing the water to the substantial exclusion of ethanol.

In another embodiment the present invention is a process for separating water from a feed mixture comprising ethanol and water which process comprises contacting the mixture at adsorption conditions with an adsorbent comprising corn meal which process comprises the steps of: (a) maintaining a plurality of chambers containing the adsorbent serially connected by connecting conduits, the chambers comprising three sections, an adsorption section, a flush section and a reload section, each section comprising one or more whole chambers and having separate operational functions occurring therein; (b) maintaining net liquid flow in a single direction through the adsorption section and the flush section only; (c) maintaining the adsorption section defined by chambers located between a feed inlet stream at the upstream boundary of the section and a raffinate outlet stream at the downstream boundary of the section; (d) maintaining the flush section upstream from the adsorption section, the flush section having the operational function of displacing ethanol from the chambers in the flush section with water, the flush section defined by at least a portion of the chambers located between a water inlet stream at an upstream boundary of the flush section and the feed inlet stream; (e) passing the feed mixture into the adsorption section at adsorption conditions to effect the selective adsorption of water by the corn meal and withdrawing a raffinate outlet stream from the adsorption zone, the ethanol concentration in the outlet stream being greater than the ethanol concentration in the feed mixture; (f) periodically advancing through the chambers, in a downstream direction with respect to the net fluid flow, all streams, including the feed inlet stream, raffinate outlet stream, and water inlet stream to effect the shifting of sections through the chambers, the operational function of the chambers comprising the reload section prior to the advancement changing to the furthermost downstream chambers of the adsorption section subsequent to the advancement, and the operational function of a like number of chambers comprising the furthermost upstream chambers of the flush section prior to the advancement changing to the reload section subsequent to the advancement; and (g) replacing the wet corn meal with dry corn meal in the chambers comprising the reload section during the time between each periodic advancement.

In another embodiment the present invention is a process for separating water from a feed mixture comprising ethanol and water which process comprises contacting the mixture at adsorption conditions with an adsorbent comprising corn meal which process comprises the steps of: (a) maintaining net fluid flow upward through a vertical column of the adsorbent in a single direction, which column contains at least two zones, an adsorption zone and a flush zone, each zone having separate operational functions occurring therein and being serially interconnected with the terminal zones of the column connected to provide a continuous connection of the zones; (b) maintaining net flow of corn meal downward through the column; (c) maintaining the adsorption zone in the column defined by the adsorbent located between a feed inlet stream at an upstream boundary of the zone with respect to the direction of the fluid flow and the top of the column at a downstream boundary of the zone; (d) maintaining a flush zone upstream from the adsorption zone, the flush zone defined by at least a portion of the adsorbent located between the bottom of the column at an upstream boundary of the flush zone and the feed inlet stream; (e) passing the feed stream into the adsorption zone at adsorption conditions to effect the selective adsorption of water by the adsorbent in the adsorption zone and withdrawing a raffinate outlet stream from the adsorption zone, the ethanol concentration in the outlet stream being greater than the ethanol concentration in the feed mixture; (f) passing the water inlet stream into the flush zone to effect the displacement of the ethanol from the adsorbent in the flush zone; and (g) continuously introducing dry corn meal into the top of the column and withdrawing wet corn meal from the bottom of the column.

Other embodiments of the invention encompass details about feed mixtures, adsorbent properties and operating conditions, all of which are hereinafter disclosed in the following discussion of each of the facets of the present invention.

BRIEF DESCRIPTION OF THE DRAWINGS

The drawings consist of FIGS. 1 through 3.

DESCRIPTION OF THE INVENTION

Figure 1:
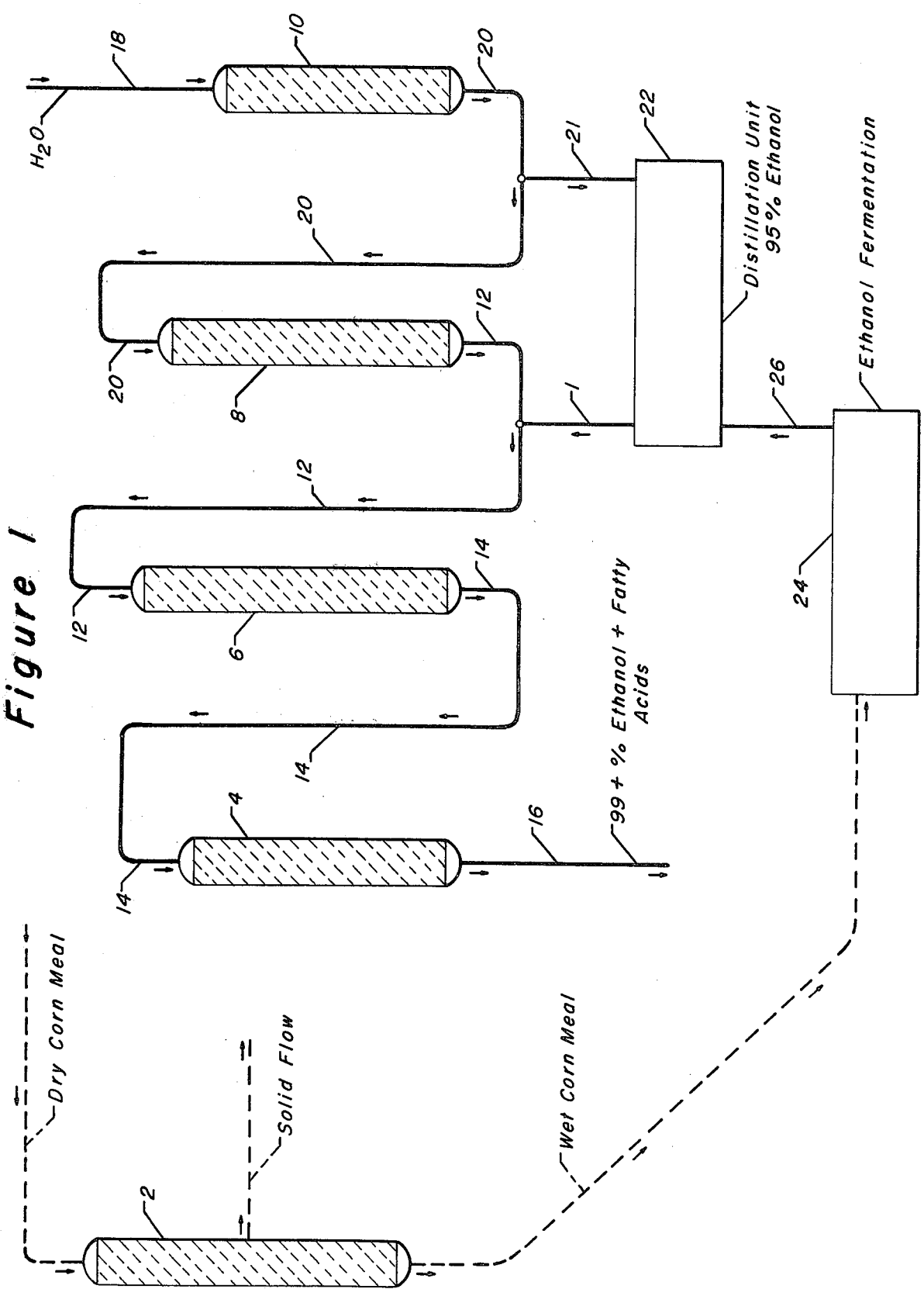
FIGS. 1 and 2 are flow diagrams of preferred embodiments of the invention.

The adsorbent used in the process of this invention comprises corn meal. Corn meal is obtained from the grinding or milling of whole corn. The corn meal is prepared for use in this invention by drying it in air at a temperature from about 50° C. to about 60° C. after it is ground.

Adsorbents in general can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

Feed mixtures to be utilized in the process of this invention will comprise a mixture of ethanol and water. To separate water from a feed mixture containing ethanol and water, the mixture is contacted with the adsorbent at adsorption conditions and the water is more selectively adsorbed and retained by the adsorbent while the ethanol is relatively unadsorbed and is removed from the interstitial void spaces between the particles of adsorbent and the surface of the adsorbent. The preferable feed mixture is that comprising about 9.5 wt. % ethanol and about 5 wt. % water which is the mixture obtained from the distillation of the product of natural fermentation of grains such as corn. Adsorption conditions preferably include a temperature within the range of from about 20° C. to about 100° C. and ambient pressure.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as a raffinate component the feed mixture component other than the selected component and the extract stream will contain the selected component as the extract component. Of course, in this invention there will only be a raffinate stream (sometimes referred to as raffinate outlet stream) because no attempt is made to remove the water extract from the adsorbent.

Although it is possible by the process of this invention to produce high purity (99% or greater) ethanol product at high recoveries, it will be appreciated that an extract component is never completely adsorbed by the adsorbent, nor is a raffinate component completely non-adsorbed by the adsorbent. The ratio of concentration of the less selectively adsorbed ethanol to the concentration of more selectively adsorbed water will be highest in the raffinate stream, next highest in the feed mixture, and lowest in the extracted material.

The adsorbent may be employed in the form of a dense compact fixed bed which is alternatively contacted with the feed mixture, flushed with water, emptied of wet adsorbent and refilled with dry adsorbent. The flushing of the bed with water enables the displacement and recovery of ethanol from the bed before it is emptied of adsorbent. In the simplest embodiment of the invention, the adsorbent is employed in the form of a single static bed in which case the process is only semicontinuous. In another embodiment a set of two or more static beds may be employed in fixed bed contacting with appropriate valving so that the feed mixture is passed through one or more adsorbent beds while the adsorbent can be reloaded in one or more of the other beds in the set. The flow of feed mixture may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbed bed systems and are therefore preferred for use in this separation process. In the moving bed or simulated moving bed processes the adsorption flushing and reloading operations are continuously taking place which allows both continuous production of a raffinate stream and the continual use of feed and flushing streams. Reference to FIG. 1 is now made for an explanation of the most preferred embodiment of this process known in the art as the simulated moving bed countercurrent flow system. Adsorbent comprising corn meal is contained in chambers 2, 4, 6, 8 and 10. A feed stream comprising about 95 wt. % ethanol and 5 wt. % water is passed via conduit 1 into conduit 12 which connects the outlet of chamber 8 to the inlet of chamber 6. Chambers 6 and 4 comprise the adsorption section. The liquid flows through chamber 6 and then 4 via conduit 14 in which chambers water is adsorbed. High purity ethanol product leaves the adsorption section via conduit 16. Water is passed to the inlet of chamber 10, which comprises the flush section, via conduit 18. In chamber 10 the water flushes ethanol from the corn meal into conduit 20. On the figure is shown an optional buffer section comprising chamber 8 which connects to upstream flush chamber 10 via conduit 20. When the ethanol concentration in the liquid in conduit 20 becomes diluted, i.e. less than the ethanol concentration in the feedstream, at least a portion of the liquid in conduit 20 is diverted to Distillation Unit 22. It is difficult to completely prevent diluted ethanol appearing in conduit 20 from continuing downstream, and for that reason it is preferred to have present the buffer section comprising chamber 8 so as to insure that diluted ethanol will not pass into the adsorption section. Distillation Unit 22 is the source of the feedstream which leaves Distillation Unit 22 via conduit 1.

Periodically, and at times no later than when the concentration of ethanol product in conduit 16 falls below a desired level, all inlet and outlet streams are advanced through the chambers in a downstream direction with respect to the net fluid flow, thereby effecting the shifting of the sections through the chambers and simulating solid flow of the adsorbent in the direction indicated on FIG. 1. Thus, what had previously been the reload section comprising chamber 2 would, after the shift, be the furthermost downstream chamber of the adsorption section, what had previously been the flush section comprising chamber 10 would be the reload section, and what had previously been the buffer section comprising chamber 8 would be the flush section. In the time between each shift the reload section comprising chamber 2 would be emptied of wet corn meal and filled with dry corn meal. The wet corn meal would be used in Ethanol Fermentation Unit 24 the product from which would be passed to Distillation Unit 22 via conduit 26, which would distill the fermentation product to obtain a distillation product comprising the feed mixture.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, water input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

Figure 2:
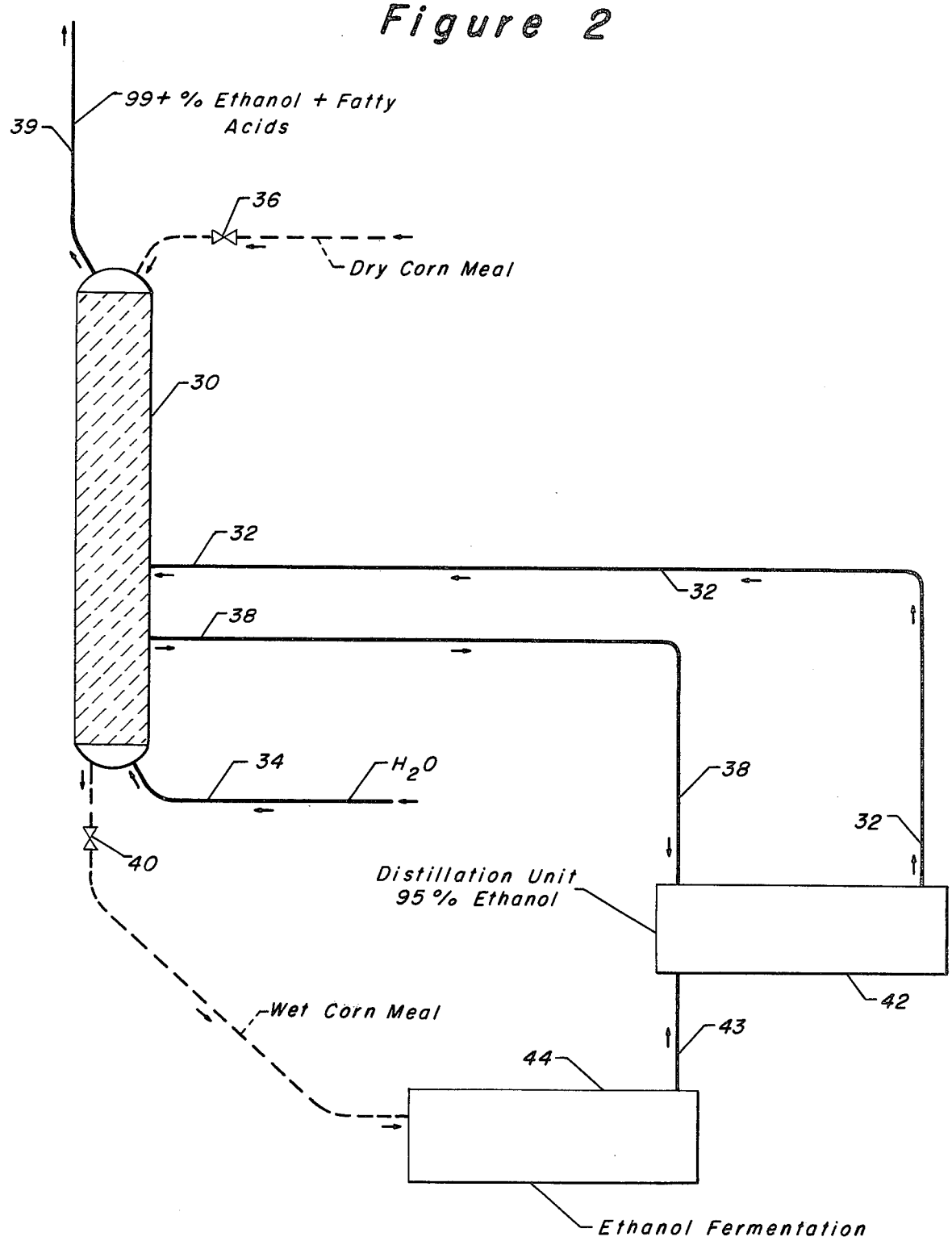

Reference is now made to FIG. 2 for explanation of another preferred embodiment of this process. This embodiment employs single vertical column 30 having feed stream inlet line 32, water inlet line 34, dry corn meal inlet means 36, raffinate outlet line 39, diluted ethanol outlet line 38 and wet corn meal outlet means 40. Column 30 is filled with corn meal and there is a net liquid flow upward through the column. The adsorption zone of the column comprises the adsorbent between the feed stream inlet as an upstream boundary and the top of the column as a downstream boundary. The flush zone of the column comprises at least a portion of the adsorbent between the bottom of the column, as an upstream boundary, and the feed stream inlet. The flush zone will preferably not extend as far downstream as the feed stream inlet so as to avoid dilution of the feed. The feedstream, comprising about 95 wt. % ethanol and 5 wt. % water, passes into the adsorption zone of column 30 via line 32. Adsorption of water occurs as the liquid passes up through the adsorption zone and the raffinate outlet stream that exists via line 39 comprises in excess of 99 wt. % ethanol.

Dry corn meal is continuously introduced into column 30 via inlet means 36 and wet corn meal withdrawn via outlet means 40 thereby effecting a moving bed of corn meal from the top to the bottom of the column countercurrent to the rising liquid. The corn meal is added and withdrawn at rates which are adjusted to maintain the desired level of ethanol concentration in the raffinate outlet stream.

The source of the feedstream is preferably Distillation Unit 42 which distills the product of Ethanol Fermentation means 44 passed to Distillation Unit 42 via conduit 43. It is the wet corn meal that is loaded into Ethanol Fermentation means 44 thereby becoming the source of the ethanol.

It is preferred to utilize a dilute ethanol outlet stream, withdrawn from column 30 upstream of the feed inlet stream and passed to Distillation Unit 42 via line 38. The dilute ethanol outlet stream enables thorough flushing of the adsorbent with the water from inlet line 34 since any desired rate of water may be passed through line 34 as long as similar rate of dilute ethanol stream is withdrawn through line 38. The dilute ethanol stream is passed to Distillation Unit 42 for recovery of the ethanol. The use of the dilute ethanol outlet stream creates a buffer zone between the outlet of that stream and the feedstream inlet. This buffer zone is useful in that it provides a margin of safety with regard to the avoidance of dilution of ethanol in the adsorption zone.

The raffinate outlet stream will contain a small amount of fatty acids leached from the corn meal. These fatty acids probably render the raffinate output stream unsuitable for use in gasohol. Fortunately, there are relatively simple methods known to the art for the removal of fatty acids from ethanol. One particularly effective method is to mix a hydrocarbon liquid with the raffinate outlet stream, particularly a hydrocarbon liquid containing saturated hydrocarbons. A portion of the hydrocarbons tend to form a precipitate with the fatty acids which is easily filtered out, thereby enabling the obtaining of a product mixture of reduced fatty acid content. The weight ratio of raffinate outlet stream to hydrocarbon liquid is preferably about 1.0:9.0. The filtered product mixture might be useful directly, for example as gasohol, when the hydrocarbon liquid used is unleaded gasoline, or could be distilled by conventional methods to recover high purity ethanol.

EXAMPLE

Figure 3:
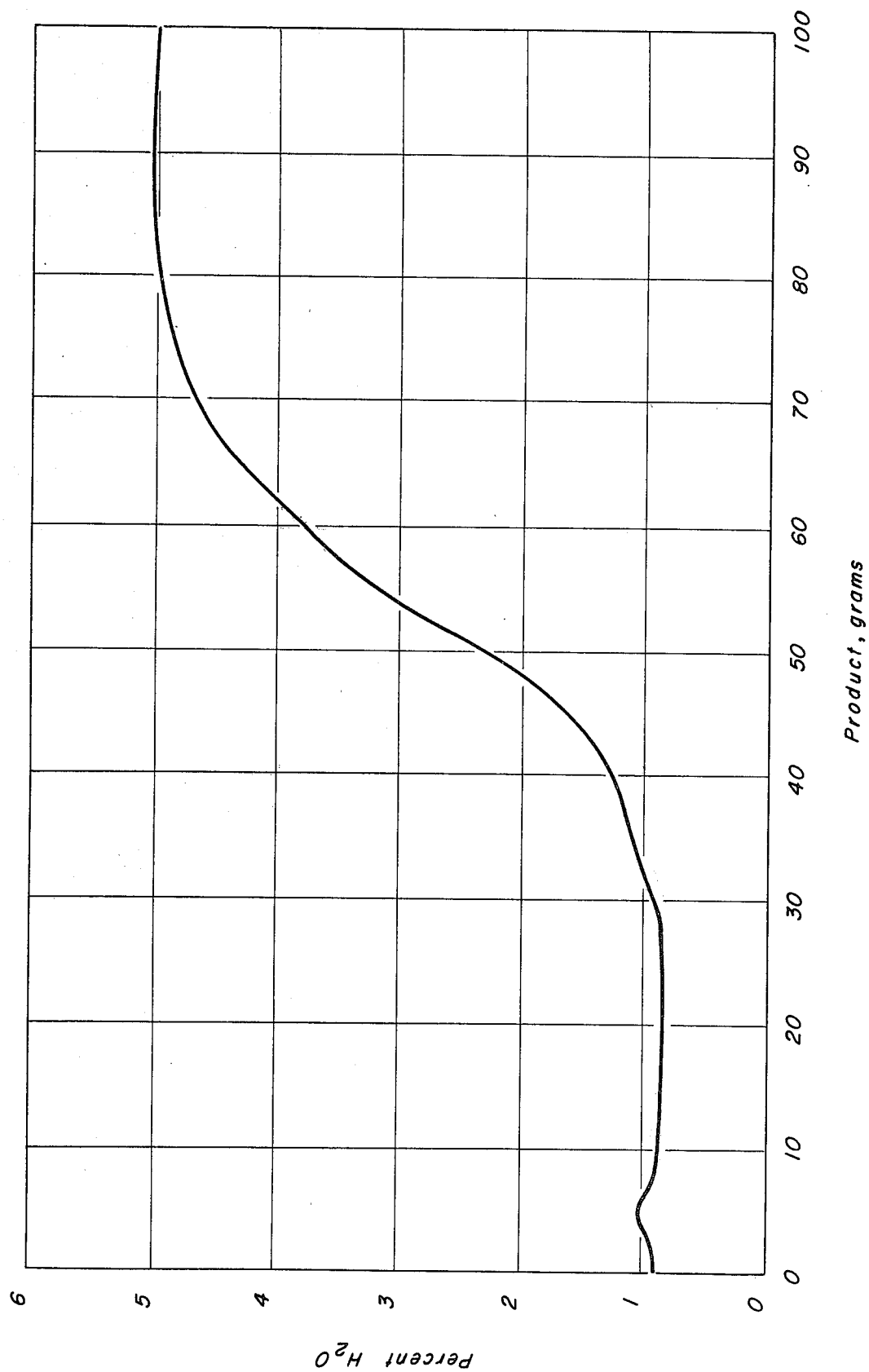
FIG. 3 is a graphical presentation of the data of the Example.

This example presents data obtained which illustrates the selectivity of corn meal for water in a water-ethanol mixture. A ten foot high plastic column was filled about 75% full with 100.0 gms. of corn meal dried at 55° C. A blend of 95% ethanol/5% water by weight was passed downflow through the column at about 1 LHSV and the effluent collected in vials for later G.C. analysis. Except for a piece of aluminum foil around the neck of the vial, no precautions were taken to exclude air during sample collections. The test was continued until the effluent equaled 95% ethanol/5% water. The resulting graph of the water content appears in FIG. 3. The average purity during the first 30 gms. of product was 99.1% ethanol by weight. The total water adsorbed during the test was about 2.25 gms. which gives a water absorption capacity of the corn meal of about 2.25% by weight under these conditions. A similar test run on a sample dried at 60° C. resulted in a product of 99.5% ethanol by weight. Again in this experiment no precautions were taken to exclude air.

The product ethanol contained yellow impurities. Upon blending this ethanol 10%/90% with n-heptane, a precipitate formed. After filtering the n-heptane ethanol mixture still contained some yellow color. A sample of this blend was analyzed and the remaining fatty acid portion still in solution was found to contain approximately 10% palmitic acid, 20% oleic acid, 40% linoleic acid, and 30% of what is believed to be linolenic acid. The precipitate was found to be mainly triacylglycerol. The fatty acids and triacylglycerols averaged 3.7% by weight of the ethanol product, about 75% of this is filtered out after addition of the n-heptane.

From the above data, 99+% purity indicates a selectivity for H₂O/ethanol large enough to meet standards for production of gasohol. Also, the purity could be improved somewhat by protecting the product collection system from moisture in the air. The capacity of the system must be large enough to adsorb as much or more water than is present in the volume of 95% ethanol that can be made from that quantity of corn. Currently 9.5 l. of ethanol can be made from 25.4 kg. of corn. To adsorb the 475 gms. of H₂O in the 9.5 l. of 95% ethanol, the corn must have a capacity of about 1.9%. The measured capacity of 2.25% indicates that about 20% of the corn used for fermentation would not have to be used to adsorb water and therefore would not have to be dried.

What is claimed is:

1. A process for separating water from a feed mixture comprising ethanol and water which process comprises contacting at adsorption conditions said mixture with an adsorbent consisting essentially of corn meal which process comprises the steps of:
    (a) maintaining a plurality of chambers containing said adsorbent serially connected by connecting conduits, said chambers comprising three sections, an adsorption section, a flush section and a reload section, each section comprising one or more whole chambers and having separate operational functions occurring therein:
    (b) maintaining net liquid flow in a single direction through said adsorption section and said flush section;
    (c) maintaining said adsorption section defined by chambers located between a feed inlet stream at the upstream boundary of said section and a raffinate outlet stream at the downstream boundary of said section;
    (d) maintaining said flush section upstream from said adsorption section, said flush section having the operational function of displacing ethanol from the chambers in the flush section with water, said flush section defined by at least a portion of the chambers located between a water inlet stream at an upstream boundary of said flush section and said feed inlet stream;
    (e) passing said feed mixture into said adsorption section at adsorption conditions to effect the selective adsorption of water by said corn meal and withdrawing a raffinate outlet stream from said adsorption zone, the ethanol concentration in said outlet stream being greater than the ethanol concentration in said feed mixture;
    (f) periodically advancing through said chambers in a downstream direction with respect to said net fluid flow all streams, including the feed inlet stream, raffinate outlet stream, and water inlet stream to effect the shifting of sections through said chambers, the operational function of the chambers comprising said reload section prior to said advancement changing to the furthermost downstream chambers of said adsorption section subsequent to said advancement, and the operational function of a like number of chambers comprising the furthermost upstream chambers of said flush section prior to said advancement changing to the reload section subsequent to said advancement; and
    (g) replacing the wet corn meal with dry corn meal in the chambers comprising the reload section during the time between each periodic advancement.

2. The process of claim 1 wherein said feed mixture comprises about 95 wt. % ethanol and about 5 wt. % water.

3. The process of claim 2 wherein the method of drying said dry corn meal comprises drying in air at a temperature of from about 50° C. to about 60° C.

4. The process of claim 1 wherein said adsorption conditions include a temperature within the range of from about 20° C. to about 100° C. and ambient pressure.

5. The process of claim 1 wherein each periodic advancement is effected no later than the occurrence of reduction of ethanol concentration in the extract stream to less than a desired level of ethanol concentration.

6. The process of claim 2 wherein the source of said feed mixture comprises a distillation unit which distills the fermentation product of wet corn meal periodically removed from said reload section.

7. The process of claim 6 wherein an additional buffer section comprising at least one chamber is located between said adsorption section and said flush section, the liquid stream flowing in the conduit between said flush and said buffer sections being diverted to an outlet stream to said distillation unit during the time the ethanol concentration of said liquid stream in said conduit is less than the concentration of ethanol in said feed mixture.

8. A process for separating water from a feed mixture comprising ethanol and water which process comprises contacting at adsorption conditions said mixture with an adsorbent consisting essentially of corn meal which process comprises the steps of:
   (a) maintaining net liquid flow upward through a vertical column of said adsorbent in a single direction, which column contains at least two zones, an adsorption zone and a flush zone, each zone having separate operational functions occurring therein and being serially interconnected with the terminal zones of said column connected to provide a continuous connection of said zones;
   (b) maintaining net flow of corn meal downward through said column;
   (c) maintaining said adsorption zone in said column defined by the adsorbent located between a feed inlet stream at an upstream boundary of said zone with respect to the direction of said fluid flow and the top of said column at a downstream boundary of said zone;
   (d) maintaining a flush zone upstream from said adsorption zone, said flush zone defined by at least a portion of the adsorbent located between the bottom of said column at an upstream boundary of said flush zone and said feed inlet stream;
   (e) passing said feed stream into said adsorption zone at adsorption conditions to effect the selective adsorption of water by said adsorbent in said adsorption zone and withdrawing a raffinate outlet stream from said adsorption zone, the ethanol concentration in said outlet stream being greater than the ethanol concentration in said feed mixture;
   (f) passing said water inlet stream into said flush zone to effect the displacement of said ethanol from the adsorbent in said flush zone; and
   (g) continuously introducing dry corn meal into the top of said column and withdrawing wet corn meal from the bottom of said column.

9. The process of claim 8 wherein said feed mixture comprises about 95 wt. % ethanol and about 5 wt. % water.

10. The process of claim 9 wherein the method of drying said dry corn meal comprises drying in air at a temperature of from about 50° C. to about 60° C.

11. The process of claim 8 wherein said adsorption conditions include a temperature within the range of from about 20° C. to about 100° C. and ambient pressure.

12. The process of claim 8 wherein the rates of introduction and withdrawal of said corn meal from said column are adjusted to maintain the desired level of ethanol concentration in said raffinate outlet stream.

13. The process of claim 8 wherein the source of said feed mixture comprises a distillation unit which distills the fermentation product of wet corn meal withdrawn from the bottom of said column.

14. The process of claim 13 wherein a buffer zone is maintained between said flushing zone and said adsorption zone, the upstream boundary of said zone being a dilute ethanol outlet stream and the downstream boundary of said zone being the feed stream inlet, said dilute ethanol outlet stream being passed to said distillation unit.

15. The process of either of claims 2 or 9 wherein fatty acids contained in said raffinate outlet stream are removed by mixing said stream with hydrocarbon liquid to obtain a product mixture, thereby effecting the formation of a precipitate containing said fatty acids, which precipitate is then filtered from said product mixture to obtain a product mixture of reduced fatty acid content.

16. The process of claim 15 wherein the weight ratio of raffinate outlet stream to hydrocarbon liquid is about 1.0:9.0.

17. The process of claim 16 wherein said hydrocarbon liquid comprises unleaded gasoline, said product mixture thereby comprising gasohol.

* * * * *